United States Patent [19]

Arant

[11] 4,139,946
[45] Feb. 20, 1979

[54] MECHANISM FOR ALIGNING TRANSFER FACE BOW TO A DENTAL ARTICULATOR

[76] Inventor: Gene W. Arant, 2444 Jupiter Dr., Los Angeles, Calif. 90046

[21] Appl. No.: 794,089

[22] Filed: Jun. 15, 1977

[51] Int. Cl.² .............................................. A61C 11/00
[52] U.S. Cl. ........................................................ 32/32
[58] Field of Search ...................................... 32/32, 20

[56] References Cited

U.S. PATENT DOCUMENTS

| 1,320,583 | 11/1919 | Stanbrough | 32/32 |
| 1,753,965 | 4/1930 | Ralph | 32/32 |
| 3,052,030 | 9/1962 | Spence | 32/20 |
| 3,552,020 | 1/1971 | Weber | 32/32 |
| 3,896,550 | 7/1975 | Lee | 32/32 |

Primary Examiner—Louis G. Mancene
Assistant Examiner—John J. Wilson

[57] ABSTRACT

A mechanism on a dental articulator for receiving and supporting the pointers of a transfer face bow in aligned relationship therewith and without disturbing the face width adjustment of the transfer face bow.

4 Claims, 5 Drawing Figures

MECHANISM FOR ALIGNING TRANSFER FACE BOW TO A DENTAL ARTICULATOR

RELATED APPLICATION

The invention disclosed and claimed herein has been disclosed in my prior copending application Ser. No. 558,284, filed Mar. 24, 1975, now United States Pat. No. 4,045,872.

BACKGROUND OF THE INVENTION

In transferring casts to a dental articulator it is necessary to use a transfer face bow to establish an identifiable three-dimensional relationship to the head of the patient. The transfer face bow conventionally includes a pair of pointers which engage respective lateral sides of the patient's head, each pointer being adjusted in its final position so that its pointed end bears upon a small tattoo mark which indicates the location of the terminal hinge axis. In conventional transfer face bows, however, when the pointers have reached their final positions of adjustment they are not collinear with each other. Therefore, in aligning the transfer face bow with the articulator, any change or adjustment in the lateral separation of the pointers which represents the face width of the patient would result in a measurement error.

Accordingly, the articulator is provided with adjustable means for enlarging or diminishing its simulated face width, so that it may be aligned with the transfer face bow without having to adjust the pointers of the face bow. The present invention provides such an adjustment mechanism, which differs in its specific details from the comparable mechanisms of the prior art.

Thus, the object and purpose of the present invention is to provide a specific mechanism for aligning a transfer face bow to an articulator, which operates in a different manner from the prior art devices used for this purpose.

DRAWING SUMMARY

DETAILED DESCRIPTION

Figure 1:
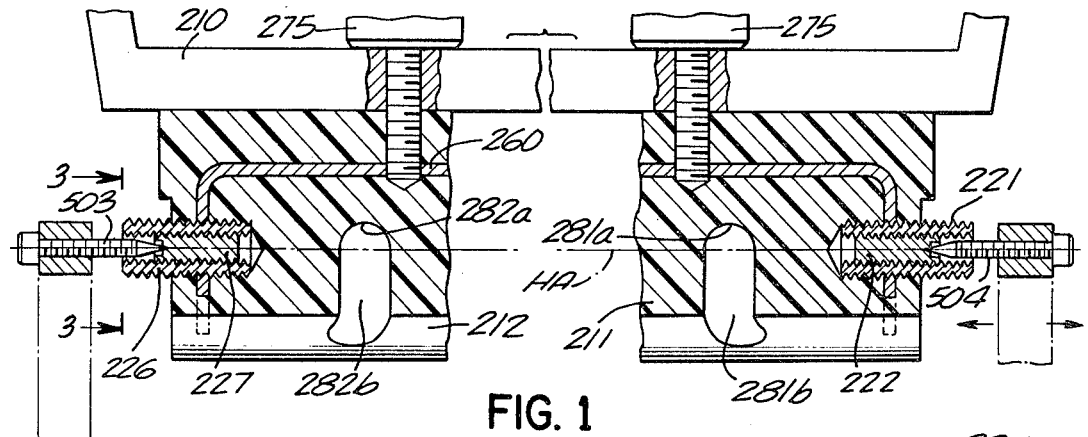
FIG. 1 is a cross-sectional elevational view of a dental articulator incorporating my new mechanism.
Figure 4:
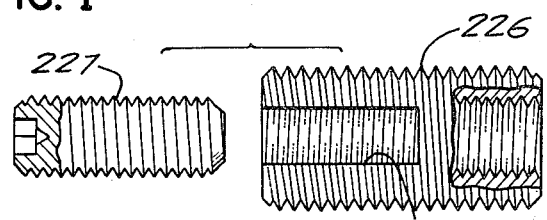
FIG. 4 is an exploded view, partially in cross-section, of the threaded tubes and threaded plugs of the analog module.
Figure 2:
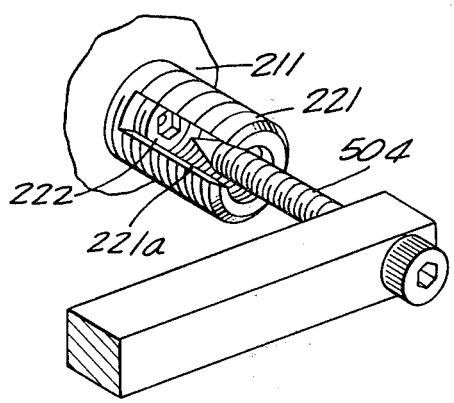
FIG. 2 is an enlarged perspective view showing attachment of a transfer face bow pointer to the analog module.
Figure 3:
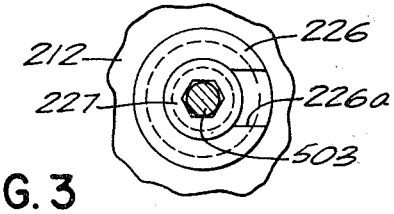
FIG. 3 is a fragmentary view, partially in cross-section taken on line 3—3 of FIG. 1.

In brief, the mechanism of the present invention includes tubular members 221, 226 which are supported upon and extend laterally outwardly from the corresponding fossae of the articulator. The longitudinal axes of the tubular members are collinear and represent the end portions of the terminal hinge axis of the articulator. Inside the tubular members are threaded nuts 222, 227, respectively. Each threaded nut on its outer end has a conical recess located at its longitudinal axis. See FIGS. 2 and 4. The purpose of this recess is to receive the pointed end of a corresponding pointer of the transfer face bow. Each threaded nut also has wrench-engaging means upon its outer end, illustrated in the drawings, FIGS. 2–4 as a hexagonal socket, for receiving an Allen wrench. At least one of the tubular members has a circumferential portion of its outer end removed. In the drawing illustration tubular member 221 has a window or slot 221a formed therein while tubular member 226 has a window or slot 226a formed therein.

Figure 5:
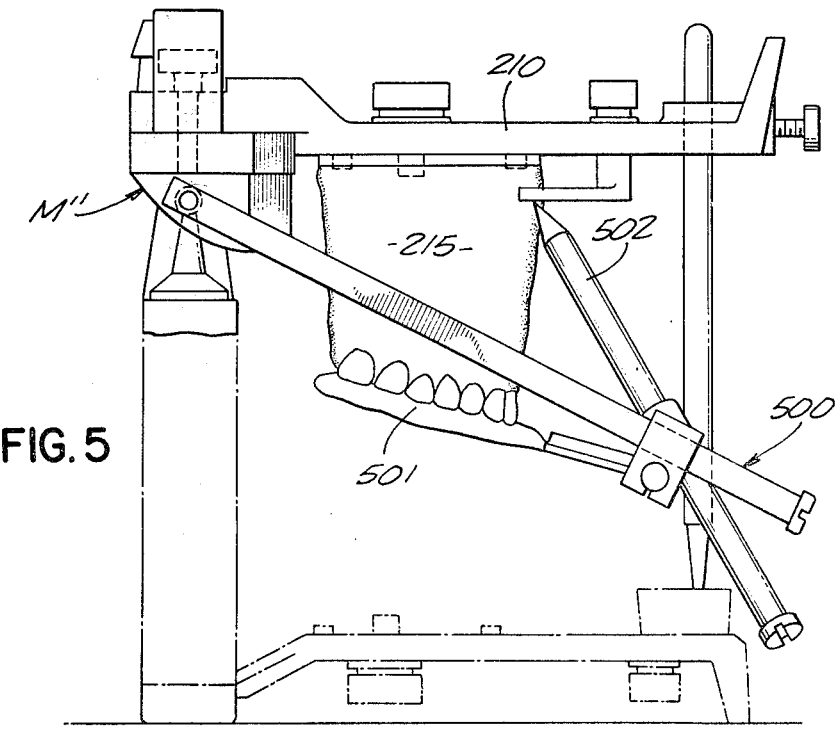
FIG. 5 is a plan view of the completed articulator set up including an upper dental cast mounted thereon.

A transfer face bow 500 (FIG. 5) may be used for aligning the cast. This is a conventional transfer face bow which is not capable of accomplishing a face width adjustment, except by loss of measurement accuracy. It has a bite plate 501, orbital pointer 502, and axis pointers 503, 504. When taking an impression from the patient on bite plate 501 the axis pointers 503, 504 are not necessarily collinear, but will in general have different axes. The pointer 504 is moved laterally through the opening 221a in the side wall of threaded tube 221. This avoids the necessity of lengthening or shortening the pointer 504 with the resultant loss of accuracy which would then occur. When the proper depth of the pointer is determined, set screw 222 is adjusted accordingly, using an allen wrench. The same procedure is followed with pointer 503. The side frames of the transfer face bow 500 are deflected slightly outwardly upon reinserting the pointers into the tubes and hooking them into the respective set screws.

In operation, the window or slot in one or both of the tubular members permits the pointers of the transfer face bow to be inserted into the outer ends of the tubular members, without the necessity of disturbing the adjustment of the pointers. A suitable wrench means is used to adjust the position of each threaded nut inside its corresponding threaded tube, to provide a simulated face width corresponding to the setting of the transfer face bow and at the same time to maintain lateral symmetry of the instrument.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. In a dental articulator having a pair of fossae for simulating the socket portions of the temporomandibular joints, a mechanism for aligning to the articulator a transfer face bow that includes a pair of pointers whose pointed ends represent the location of the terminal hinge axis on the sides of a patient's face, said mechanism comprising:

a pair of tubular members supported upon and projecting laterally outwardly from respective ones of the articulator fossae, said tubular members having longitudinal axes which are collinear and which represent corresponding end portions of the hinge axis of the articulator;

said tubes being internally threaded, and the outwardly projecting end of at least one of said tubes having a slot therein, whereby the pointed ends of the pointers may be inserted within the ends of the tubular members without disturbing the adjustment of the pointers; and a pair of threaded nuts carried within the ends of respective ones of said tubular members in threaded engagement therewith, the outer end face of each of said nuts having a recess on its longitudinal axis for receiving the pointed end of a corresponding pointer, and the outer end of each nut further having wrench-engaging means for permitting the lateral spacing between said nuts to be adjusted to conform to the lateral spacing between the pointed ends of the pointers.

2. The mechanism of claim 1 wherein each of said tubular members has a circumferential portion removed from its outer end.

3. The mechanism of claim 1 wherein said wrench-engaging means is a hexagonal socket.

4. The mechanism of claim 1 wherein said recess is of conical configuration.

* * * * *